United States Patent [19]

Groenke

[11] Patent Number: 5,701,891
[45] Date of Patent: Dec. 30, 1997

[54] OLEFIN HEAT AND MOISTURE EXCHANGER

[75] Inventor: Allen W. Groenke, Bloomington, Minn.

[73] Assignee: Nellcor Puritan Bennett Incorporated, Pleasanton, Calif.

[21] Appl. No.: 566,086

[22] Filed: Dec. 1, 1995

[51] Int. Cl.$^6$ .................. A61M 16/10; B01D 27/07; B01D 29/07

[52] U.S. Cl. .................. 128/205.29; 128/201.13; 261/112.1; 261/112.2

[58] Field of Search .................. 128/205.29, 201.13; 261/112.1, 112.2

[56] References Cited

U.S. PATENT DOCUMENTS

| | | | |
|---|---|---|---|
| 2,019,186 | 10/1935 | Kaiser | 261/112.2 |
| 2,610,038 | 9/1952 | Phillips | 257/245 |
| 3,265,550 | 8/1966 | Lindqvist | 261/112.2 |
| 3,347,381 | 10/1967 | Minch et al. | 261/112.2 |
| 3,466,151 | 9/1969 | Sicard et al. | 261/112.2 |
| 3,747,598 | 7/1973 | Cowans | 128/142 |
| 4,054,980 | 10/1977 | Roma | 29/157.3 |
| 4,069,028 | 1/1978 | Brown | 62/3 |
| 4,124,478 | 11/1978 | Tsien et al. | 204/255 |
| 4,258,784 | 3/1981 | Perry et al. | 165/166 |
| 4,294,242 | 10/1981 | Cowans | 128/201.13 |
| 4,325,365 | 4/1982 | Barbuto | 128/201.13 |
| 4,332,135 | 6/1982 | Barclay et al. | 62/3 |
| 4,411,310 | 10/1983 | Perry et al. | 165/166 |
| 4,432,409 | 2/1984 | Steele | 165/8 |
| 4,512,392 | 4/1985 | van Ee et al. | 165/54 |
| 4,577,678 | 3/1986 | Franenfeld et al. | 165/10 |
| 4,733,718 | 3/1988 | Schikowsky et al. | 165/4 |
| 4,744,414 | 5/1988 | Schon | 165/167 |
| 4,817,708 | 4/1989 | Ono et al. | 165/54 |
| 4,858,685 | 8/1989 | Szucs et al. | 165/166 |
| 4,875,520 | 10/1989 | Steele et al. | 165/10 |
| 4,955,435 | 9/1990 | Shuster et al. | 165/170 |
| 5,320,096 | 6/1994 | Hans | 128/205.29 |
| 5,339,653 | 8/1994 | DeGregoria | 62/467 |

OTHER PUBLICATIONS

K. Prasad, M.D. et al., "Heat & Moisture Exchangers (HME's): Physics, Function and Efficacy–How Do they Work? Are They All Created Equal?", Beth Israel Medical Center, Department of Anesthesiology, date prior to or even with Oct. 27, 1995, 4 pages.

R. Branson et al., "Humidification in the Intensive Care Unit", *Clinical Investigations in Critical Care*, Dec., 1993, 7 pages.

I. Cohen, M.D. et al., "Endotracheal Tube Occlusion Associated with the Use of Heat and Moisture Exchangers in the Intensive Care Unit," *Critical Care Medicine*, vol. 16, No. 3, Mar., 1988, 3 pages.

R. Branson et al., "Laboratory Evaluation of Moisture Output of Seven Airway Heat and Moisture Exchangers," *Respiratory Care*, vol. 32, No. 9, Sep., 1987, 3 pages.

W. Pratt, Jr. et al., "A Continuous Demagnetization Refrigerator Operating Near 2K and a Study of Magnetic Refrigerants," *Cryogenics*, Dec., 1977, 3 pages.

G.V. Brown, "Magnetic Heat Pumping Near Room Temperature," *Journal of Applied Physics*, vol. 47, No. 8, Aug., 1976, pp. 3673–3680.

A.J. DeGregoria et al., "Test Results of an Active Magnetic Regenerate Refrigerator," *Advances in Cryogenic Engineering*, vol. 37, Part B., 1992, pp. 875–882.

(List continued on next page.)

*Primary Examiner*—Vincent Millin
*Assistant Examiner*—Robert Weiland
*Attorney, Agent, or Firm*—Nawrocki, Rooney & Sivertson

[57] ABSTRACT

A heat exchanger medium which can be incorporated into a heat and moisture exchanger. The heat exchanger medium includes an elongate sheet of spunbonded olefin. The sheet has a longitudinal axis, a front and back surface and first and second edges generally parallel to the longitudinal axis of the sheet. The sheet may be covered with a hydrophilic coating and a desiccant.

21 Claims, 2 Drawing Sheets

OTHER PUBLICATIONS

R. Farris, "Rubber Heat Engines, Analyses and Theory," *Polymer Engineering and Science*, vol. 17, No. 10, Oct., 1977, pp. 737–744.

L. Treloar, *The Physics of Rubber Elasticity*, Second Edition, Oxford at the Clarendon Press, 1956, 3 pages.

R. Hay, M.D. et al., "Efficacy of a New Hygroscopic Condenser Humidifier," *Critical Care Medicine*, vol. 10, No. 1, Jan., 1982, 5 pages.

C. Martin, M.D. et al., "Performance Evaluation of Three Vaporizing Humidifiers and Two Heat and Moisture Exchangers in Patients with Minute Ventilation> 10L/Min.", *Chest*, Sainte Marguerite Hospital, University of Marseilles, Marseilles Medical School, Nov., 1992, pp. 1347–1350.

B. Eckerbom et al., "Performance Evaluation of Six Heat and Moisture Exchangers According to the Draft International Standard (ISO/DIS 9360)", *Acta Anaesthesiol Scand*, vol. 34, 1990, pp. 404–408.

P. Bickler, M.D., et al. "Efficiency of Airway Heat and Moisture Exchangers in Anesthetized Humans," *Anesth Analg*, vol. 71, 1990, pp. 415–418.

S½T. Sottiaux, M.D., et al., "Comparative Evaluation of Three Heat and Moisture Exchangers During Short–Term Postoperative Mechanical Ventilation," *Chest*, Jul., 1993, pp. 220–224.

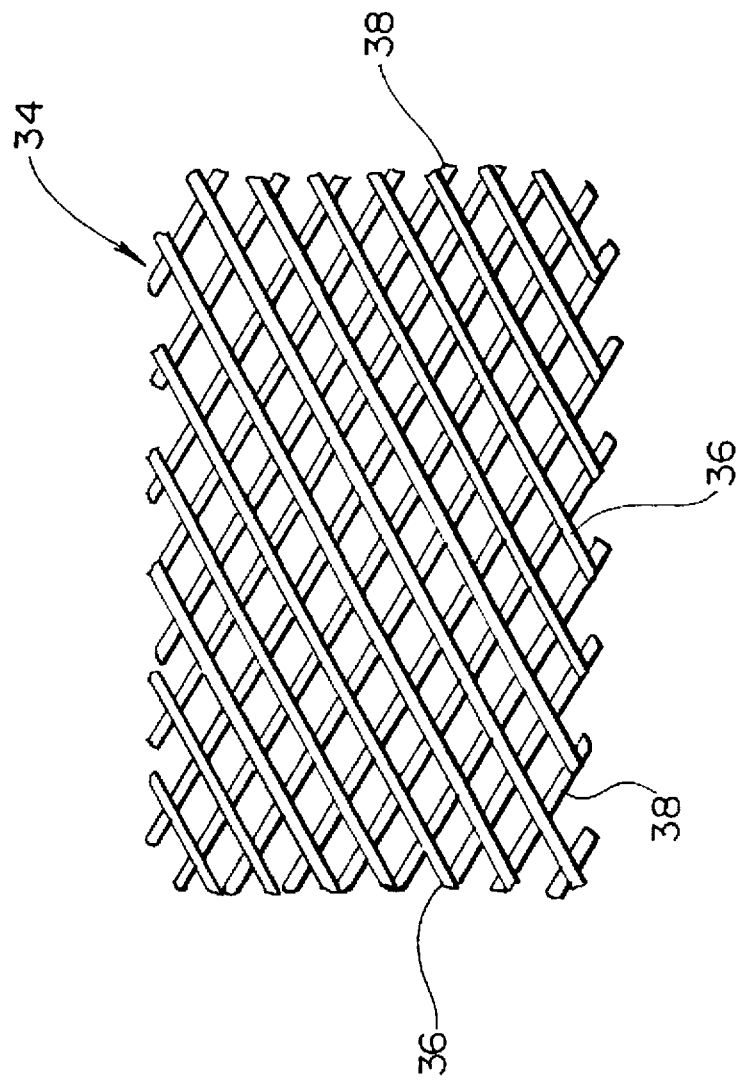

OLEFIN HEAT AND MOISTURE EXCHANGER

BACKGROUND OF THE INVENTION

The present invention pertains generally to the field of heat exchangers and, in particular, to heat moisture exchangers used in respiratory therapies.

Humidification and warming of inspired gases are generally necessary when therapeutic respiratory devices are used. The temperature and humidity of the gas introduced into a patient from a therapeutic respiratory device should match the inspiratory conditions occurring at the point of entry into a patient's respiratory system. If the level of humidity is less than this level, a humidity deficit may be produced. If the level of humidity is greater than this, fluid overload and patient discomfort may result. High or low inspired gas temperatures can undesirably elevate or depress a patient's body temperature. Ideally, gases delivered to the nose and mouth should be heated and humidified to room conditions. For example, gases delivered to a patient's nose through a mask should preferably be at a room temperature of 22° C. and a relative humidity of 50%.

Artificial noses or heat and moisture exchangers (HME's) are common devices used to passively heat and humidify inspired gas. HME's collect heat and moisture from a patient's expired gas and return it to the patient during the following inspiration. Most HME devices include both a heat exchanger for storing heat from expired air, and a desiccant to retain moisture. A portion of the stored heat and moisture is returned to the patient upon inhalation.

Prior heat and moisture exchange devices included heat exchangers made from materials with relatively low heat capacity such as aluminum or steel, and relatively higher heat capacity materials such as paper. Calcium chloride and lithium chloride were used as desiccants. Although the paper heat exchangers have a desirably higher heat capacity than the metallic exchangers, they may absorb significant amounts of moisture with prolonged use. Too much accumulated moisture can increase the resistance to inhalation and exhalation through the HME. Additionally, the lithium chloride and calcium chloride may dissolve in the water condensed within the HME and drip out of the HME. Consequently, the HME could lose its moisture retaining effectiveness.

SUMMARY OF THE INVENTION

The present invention pertains to an improved heat exchanger medium, and, more particularly, to an improved heat exchanger medium which can be incorporated into a heat and moisture exchanger (HME). The heat exchanger medium of the present invention preferably is formed from an elongate sheet including spunbonded olefin. Spunbonded olefin is sometimes referred to as Tyvek™ which is formed from 0.5 to 10 micrometer non-directional spun fibers bonded by heat and pressure without binders or fillers.

The olefin sheet may be incorporated into an HME for use as a heat exchanger. The sheet may include a desiccant. The olefin sheet of the present invention can provide a heat sink which does not absorb significant amounts of moisture which undesirably increases the weight of the HME. The sheet does, however, have a high heat capacity. The spun fiber structure of the olefin also provides the sheet with a larger surface area.

Preferably, prior to incorporating the desiccant into the sheet, the sheet is coated with a hydrophilic coating such as polyvinylpyrrolidone, polyvinyl alcohol or polyacrylic acid. The desiccants which may then be incorporated into the sheet include compounds such as lithium chloride, calcium chloride or magnesium chloride. These compounds can be incorporated into the sheet by allowing the hydrophilic coating to absorb a solution containing the compound.

The olefin sheet preferably has a longitudinal axis, front and back surfaces, and first and second edges generally parallel to the longitudinal axis of the sheet. The sheet may include a plurality of corrugations extending between the first and second edges. The corrugations can include a portion which extends longitudinally and transversely relative to the longitudinal axis of the sheet, for example, the corrugations can be disposed in a herringbone pattern.

When the sheet is incorporated into a heat and moisture exchanger, the sheet is preferably disposed in a spiraling, generally cylindrically-shaped roll such that the sheet is arranged in generally concentric layers. The spiraling roll can then be placed into an enclosure of a housing including a patient port and a machine port.

A further embodiment of the heat and moisture exchanger in accordance with the present invention can include a second elongated sheet of spunbonded olefin. The second sheet also includes a longitudinal axis, front and back surfaces, and first and second edges generally parallel to the longitudinal axis of the second sheet. The second sheet can be placed back to back with the other sheet in a spiraling roll such that the corrugations of the first sheet generally do not nest in the corrugations of the second sheet.

A further embodiment of the heat and moisture exchanger in accordance with the present invention, can include an elongated sheet of netting having a longitudinal axis, front and back surfaces and first and second edges generally parallel to the longitudinal axis of the netting. The sheet of netting can be disposed between the generally concentric layers of the olefin sheet in the spiraling roll to provide a spacer therebetween.

BRIEF DESCRIPTION OF THE DRAWINGS

FIG. 5 is a view of a portion of a sheet of netting.

DETAILED DESCRIPTION OF THE INVENTION

Figure 1:
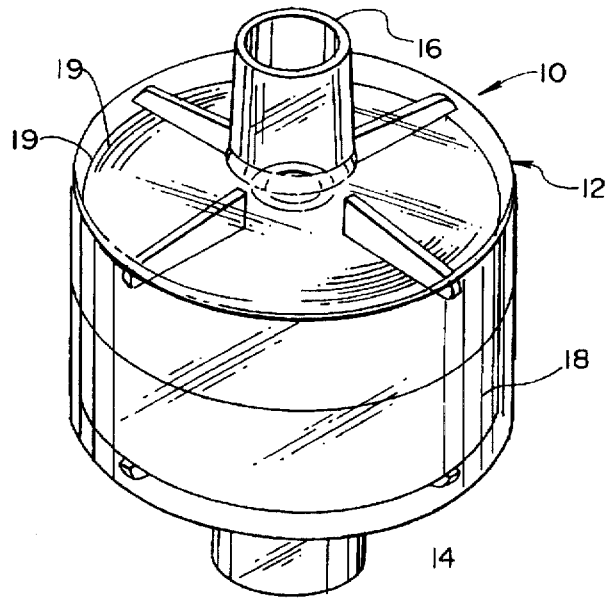
FIG. 1 is a perspective view of a heat and moisture exchanger in accordance with the present invention.

Now referring to the drawings wherein like reference numerals refer to like elements throughout the several views, FIG. 1 shows a heat moisture exchanger (HME) generally referred to by the numeral 10. HME 10 includes a housing 12 having a patient port 14 and a machine port 16. As shown, housing 12 is formed from a clear plastic. As understood in the art, however, housing 12 need not be formed from clear plastic but can be formed from any biocompatible material which can form a substantially hermetic seal.

Patient port 14 is preferably configured to receive a tube having a patient port adapter for connecting the tube to patient port 14. The end of the tube opposite the patient port adapter will be connected to a mask or other suitable means known in the art for connection to a patient. Machine port 16 is configured to be coupled to a tube connected to any of several types of respiratory machines. Patient port 14 is fluidly connected through housing 12 to machine port 16 such that gas may flow from the tube connected to the machine through HME 10 to the tube connected to the patient.

Within the HME is a heat exchanger bed or heat reservoir 18. Heat exchanger bed 18 is preferably a heat moisture exchanger bed such that the HME can be used to passively heat and humidify inspired gas. Bed 18 is preferably formed from a heat exchanger medium including an elongated spunbonded olefin sheet 19. HME 10 can then collect a patient's heat and moisture from expired gas and return a portion of the stored heat and moisture to the patient upon inhalation.

The moisture exchanging capacity of HME 10 can be enhanced by including within housing 12 a desiccant such as lithium chloride, calcium chloride, magnesium chloride, activated alumina, silica gel or some other desiccant. The desiccant can be deposited directly on sheet 19, however, sheet 19 is preferably first coated with a hydrophilic substance such as polyvinylpyrrolidone, polyvinyl alcohol or polyacrylic acid. Then sheet 19 can be dipped into a solution containing the desiccant such that the hydrophilic coating absorbs the solution including the desiccant.

Figure 2:
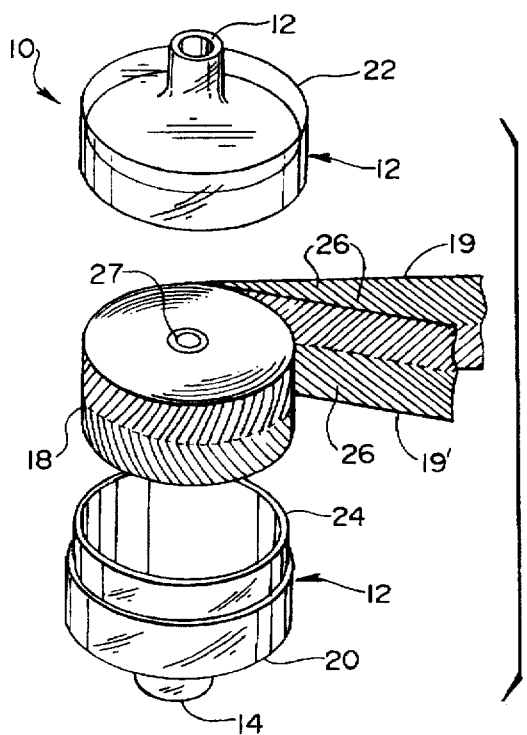
FIG. 2 is an exploded view of the heat and moisture exchanger of FIG. 1, showing heat exchanger sheets partially unrolled.

FIG. 2 is an exploded view of HME 10. Housing 12 can include two portions 20 and 22. Portion 20 can include a flange 24 insertable into portion 22 to sealably enclose heat exchanger bed 18 within housing 12.

Sheet 19 of heat exchanger bed 18 is preferably formed from spunbonded olefin sometimes referred to as Tyvek™. Sheet 19 includes a plurality of corrugations 26 therein. Corrugations 26 can extend transversely and longitudinally relative to the longitudinal axis of sheet 19, for example, in a herringbone pattern.

To form heat exchanger bed 18, sheet 19 is wrapped around a cylindrical core member or spool 27. As sheet 19 is wrapped around core member 27, corrugations 26 separate adjacent spiraling layers of sheet 19 from one another. Flow channels are defined between adjacent layers of sheet 19 and adjacent corrugations 26. A sheet 19', substantially similar to sheet 19, can be placed back to back in heat exchanger bed 18 to enhance the performance of the flow channels. This is possible by reversing the corrugation pattern of sheet 19 from 19' to avoid nesting of corrugations 26 of one layer in corrugations 26 of an adjacent layer of sheet 19.

Figure 3:
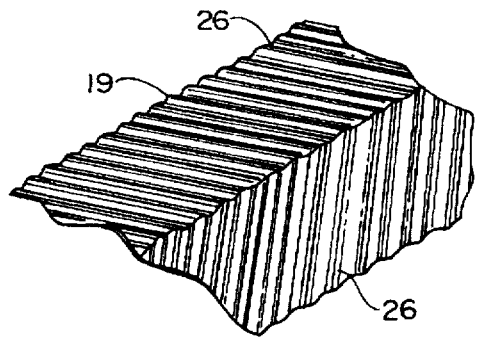
FIG. 3 is a partial view of the heat exchanger sheet including a view of the corrugations therein.

FIG. 3 is a view of a portion of sheet 19. The herringbone pattern of corrugations 26 can be seen clearly in this view.

Figure 4:
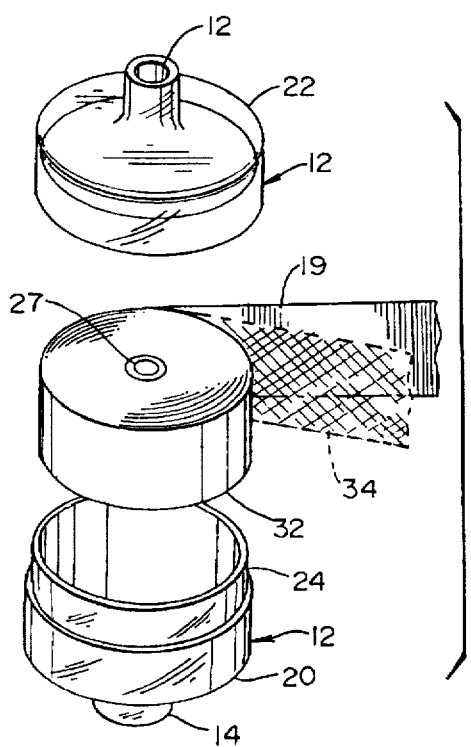
FIG. 4 is a view of a sheet of netting rolled between adjacent layers of the heat exchanger sheet.

FIG. 4 is an alternate heat exchanger bed embodiment 32. Unlike bed 18, bed 32 includes a sheet of netting 34 wound around a core member 27 between adjacent layers of spirally wound sheet 19. Strip 34 can be formed from a polymer. When netting 34 is placed within bed 32, sheet 19 need not be corrugated to provide flow channels between adjacent layers of sheet 19. Netting 34 will provide sufficient spacing between adjacent layers of sheet 19 to allow flow between the layers. Sheet 19 can, however, be corrugated even when netting 34 is placed in bed 32.

FIG. 5 is a partial view of netting 34. Netting 34 includes diagonal strands 36 and 38. Strands 36 are generally oriented in a first diagonal direction in a first plane whereas strands 38 are generally oriented in a second diagonal direction in a second plane. This bi-planar structure enables the netting to provide air passages between the adjacent layers of the heat exchanger sheet 19.

In use, patient port 14 can be connected to a tube leading to a patient's nose and/or mouth. Machine port 16 can be connected to a tube leading to a respirator. A gas can be drawn or forced through HME 12 from machine port 16 to patient port 14 and into the patient. Upon expiration, warm and moistened gas will be expired from the patient and passed through heat exchanger bed 18 from patient port 14 to machine port 16. Some of the heat from the expired gas will be absorbed by heat exchanger bed 18 and some of the expired moisture will condense on bed 18. Additional moisture can be retained if a desiccant is included within the housing 12.

EXAMPLE I

A prototype embodiment of the present invention was created and tested in accordance with the procedures found in ISO 9360. The result of the testing of this prototype found that inspired humidity was 30.7 mg $H_2O$ per liter with a pressure drop across the HME of 2.54 cm $H_2O$.

This prototype was assembled with two sheets of spunbonded olefin. Each sheet was 0.007 inches thick by 1.375 inches wide and approximately 12 feet long. The sheets of Tyvek™ were embossed with a herringbone pattern by turning them between 32 pitch herringbone gears. The two sheets were laid together with the herringbone patterns facing in opposite directions to create air passages therebetween. The sheets were then wound around a polypropylene cylinder core member. The core member had a diameter of 0.64 inches and a length of 1.375 inches. The sheets where then placed in a housing substantially similar to that shown in FIG. 1.

EXAMPLE II

A second prototype in accordance with the present invention was prepared and tested using the procedures found in ISO 9360. The test results obtained using that prototype found an inspired humidity level of 28.7 mg $H_2O$ per liter with a pressure drop of 1.57 cm $H_2O$ across the heat and moisture exchanger.

This prototype was assembled with one sheet of spunbonded olefin 0.007 inches thick by 1.375 inches wide and approximately 12 feet long. One sheet of plastic netting was placed together with the olefin sheet. The netting was 0.02 inches thick by 1.375 inches wide and approximately 12 feet long. The netting was obtained from Nalle Plastics of Austin, Tex. which identified the netting as model #LWS-SYM. The netting and the olefin sheet were wound around a polypropylene cylinder core member having a diameter of 0.64 inches and a length of 1.375 inches. The wound assembly was then placed in a housing substantially similar to that shown in FIG. 1.

Note that the olefin sheets used in both Examples I and II were DuPont Tyvek™. Tyvek™ is formed from 0.5 to 10 micrometer non-directional spun fibers bonded by heat and pressure without binders or fillers.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A heat exchanger medium, comprising:
   an elongated sheet including spunbonded olefin, the sheet having a longitudinal axis, a front surface and back surface, and a first edge and a second edge generally parallel to the longitudinal axis of the sheet, wherein the sheet includes a desiccant.

2. A heat exchanger medium in accordance with claim 1, wherein the sheet includes a hydrophilic coating selected from the group consisting of polyvinylpyrrolidone, polyvinyl alcohol, and polyacrylic acid.

3. A heat exchanger medium in accordance with claim 2, wherein the sheet including the hydrophilic coating includes a desiccant.

4. A heat exchanger medium in accordance with claim 1, wherein the sheet includes a plurality of corrugations extending between the first and second edges of the sheet.

5. A heat exchanger medium in accordance with claim 4, wherein the corrugations include a portion which extends longitudinally and transversely relative to the longitudinal axis of the sheet.

6. A heat exchanger medium in accordance with claim 5, wherein the corrugations are disposed in a herringbone pattern.

7. A heat and moisture exchanger, comprising:

a housing including an enclosure having a patient port and a machine port;

a first elongated sheet including spunbonded olefin, the sheet having a longitudinal axis, a front surface and back surface, and a first edge and a second edge generally parallel to the longitudinal axis of the sheet;

wherein the sheet is disposed in a spiraling generally cylindrically-shaped roll such that the sheet is arranged in generally concentric layers; and the roll is disposed within the housing enclosure; and an elongate sheet of netting having a longitudinal axis, a front surface and a back surface, and a first edge and a second edge generally parallel to the longitudinal axis of the sheet of netting wherein the sheet of netting is disposed between the generally concentric layers of the olefin sheet.

8. A heat and moisture exchanger in accordance with claim 7, wherein the sheet includes a desiccant.

9. A heat and moisture exchanger in accordance with claim 7, wherein the sheet includes a hydrophilic coating selected from the group consisting of polyvinylpyrrolidone, polyvinyl alcohol, and polyacrylic acid.

10. A heat and moisture exchanger in accordance with claim 9, wherein the sheet including the hydrophilic coating includes a desiccant.

11. A heat and moisture exchanger in accordance with claim 7, wherein the sheet includes a plurality of corrugations extending between the first and second edges of the sheet.

12. A heat and moisture exchanger in accordance with claim 11, wherein the corrugations include a portion which extends longitudinally and transversely to the sheet.

13. A heat and moisture exchanger in accordance with claim 12, further comprising:

a second elongated sheet of spun-bonded olefin, the sheet having a longitudinal axis, a front surface and a back surface, and a first edge and a second edge generally parallel to the longitudinal axis of the sheet, the sheet having corrugations disposed between the edges, wherein the first sheet and the second sheet are disposed back to back in the spiraling roll such that the corrugations of the first sheet generally do not nest in the corrugations of the second sheet.

14. A heat and moisture exchanger in accordance with claim 7, wherein the netting comprises a polymer.

15. A heat and moisture exchanger comprising:

a housing including an enclosure having a patient port and machine port;

an elongated heat exchanger sheet, the sheet having a longitudinal axis, a front surface and a back surface, and a first edge and a second edge generally parallel to the longitudinal axis of the sheet;

an elongate sheet of netting having a longitudinal axis, a front surface and a back surface, and a first edge and a second edge generally parallel to the longitudinal axis of the netting; and wherein the back surface of the sheet and the back surface of the netting are disposed adjacent each other in a spiraling roll such that the sheet of netting defines a spacer between generally concentric layers of the sheet; and the roll is disposed within the housing enclosure.

16. A heat and moisture exchanger in accordance with claim 15, wherein the netting comprises a polymer.

17. A heat and moisture exchanger in accordance with claim 15, wherein the sheet includes a desiccant.

18. A heat and moisture exchanger in accordance with claim 15, wherein the sheet includes a hydrophilic coating selected from the group consisting of polyvinylpyrrolidone, polyvinyl alcohol, and polyacrylic acid.

19. A heat and moisture exchanger in accordance with claim 15, wherein the sheet includes cellulose.

20. A heat and moisture exchanger in accordance with claim 15, wherein the netting includes a first plurality of strands extending at a first angle to the longitudinal axis of the netting and a second plurality of strands extending at a second angle to the longitudinal axis, the second angle not being equal to the first angle.

21. A heat and moisture exchanger in accordance with claim 20, wherein the first plurality of strands is disposed at the front surface of the netting and the second plurality of strands is disposed at the back surface of the netting.

* * * * *